United States Patent [19]
Dubrul et al.

[11] Patent Number: 5,380,273
[45] Date of Patent: Jan. 10, 1995

[54] VIBRATING CATHETER

[76] Inventors: Will R. Dubrul, P.O. Box 246, Redwood City, Calif. 94064; Michael A. Evans, 637 Webster St., Palo Alto, Calif. 94301

[21] Appl. No.: 65,470

[22] Filed: May 19, 1993

Related U.S. Application Data

[63] Continuation-in-part of Ser. No. 885,665, May 19, 1992, abandoned.

[51] Int. Cl.⁶ .............................................. A61B 17/32
[52] U.S. Cl. ........................................ 604/22; 601/2; 607/97; 606/169
[58] Field of Search ............ 128/24 AA, 898; 604/20, 604/22, 49; 606/169-171; 601/2; 627/97

[56] References Cited

U.S. PATENT DOCUMENTS

| | | | |
|---|---|---|---|
| 3,352,303 | 11/1967 | Delaney | 128/24 AA |
| 3,565,062 | 2/1971 | Kuris | 606/169 |
| 3,809,093 | 5/1974 | Abraham | 606/169 |
| 3,823,717 | 7/1974 | Pohlman et al. | 606/169 |
| 3,828,770 | 8/1974 | Kuris et al. | 128/62 A |
| 3,861,391 | 1/1975 | Antonevich et al. | 128/24 AA |
| 4,692,139 | 9/1987 | Stiles | 604/19 |
| 4,735,604 | 4/1988 | Watmough et al. | 604/22 |
| 4,808,153 | 2/1989 | Parisi | 606/169 |
| 4,815,478 | 3/1989 | Buchbinder et al. | 128/657 |
| 4,834,703 | 5/1989 | Dubrol et al. | 604/48 |
| 4,867,141 | 9/1989 | Wakada et al. | 604/22 |
| 4,870,953 | 10/1989 | Don Micheal et al. | 128/24 |
| 4,898,575 | 2/1990 | Fischell et al. | 604/22 |
| 4,920,954 | 5/1990 | Alliger et al. | 128/24 |
| 5,058,570 | 10/1991 | Idemoto et al. | 604/22 |
| 5,069,664 | 12/1991 | Guess et al. | 604/22 |
| 5,163,421 | 11/1992 | Bernstein et al. | 606/169 |
| 5,243,997 | 9/1993 | Uflacker et al. | 604/22 |
| 5,248,296 | 9/1993 | Alliger | 604/22 |

Primary Examiner—C. Fred Rosenbaum
Assistant Examiner—Michael Rafa
Attorney, Agent, or Firm—Michael G. Petit

[57] ABSTRACT

The present invention describes a catheter suitable for introduction into a tubular tissue for dissolving blockages in such tissue. The catheter is particularly useful for removing thrombi within blood vessels. In accordance with the preferred embodiments, a combination of vibrating motion and injection of a lysing agent is utilized to break up blockages in vessels. The vessels may be veins, arteries, ducts, intestines, or any lumen within the body that may become blocked from the material that flows through it. As a particular example, dissolution of vascular thrombi is facilitated by advancing a catheter through the occluded vessel, the catheter causing a vibrating, stirring action in and around the thrombus usually in combination with the dispensing of a thrombolytic agent such as urokinase into the thrombus. The catheter has an inflatable or expandable member near the distal tip which, when inflated or expanded, prevents the passage of dislodged thrombus around the catheter. The dislodged portions of thrombus are directed through a perfusion channel in the catheter, where they are removed by filtration means housed with the perfusion channel before the blood exits the tip of the catheter. Catheters that allow both low frequency (1-1000 Hz) vibratory motion and delivery of such agents to a blockage and a method for using such catheters are disclosed.

4 Claims, 5 Drawing Sheets

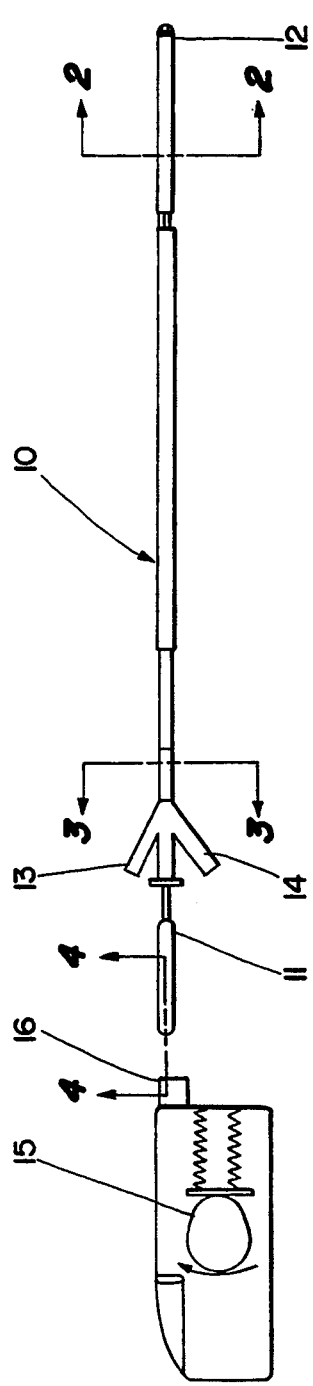
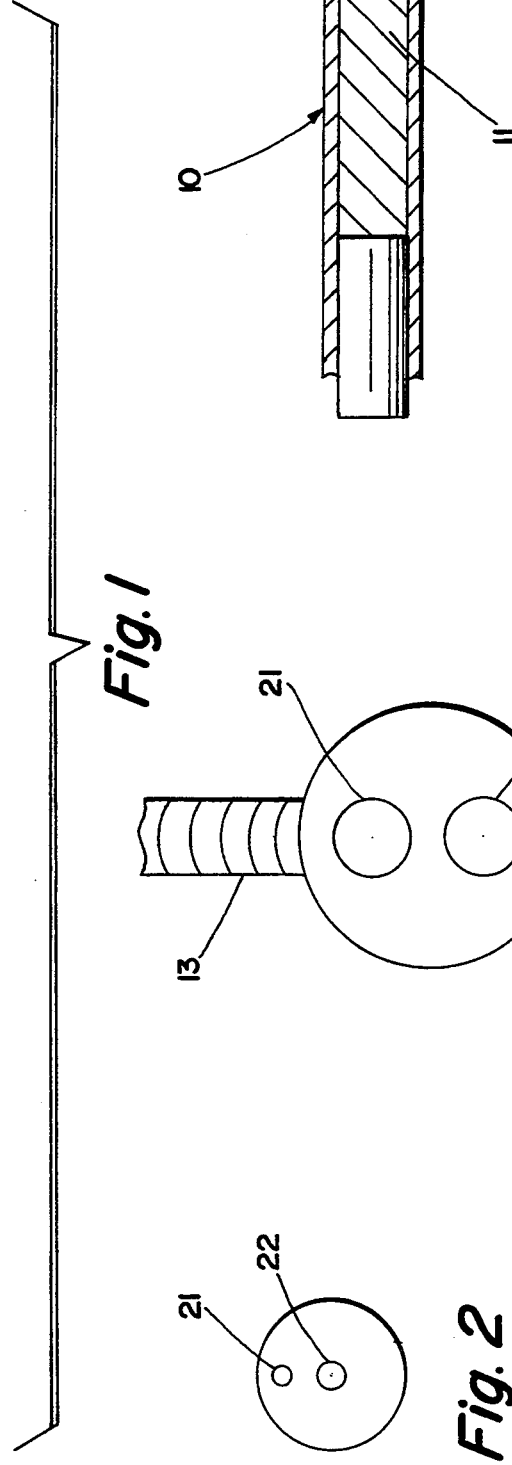
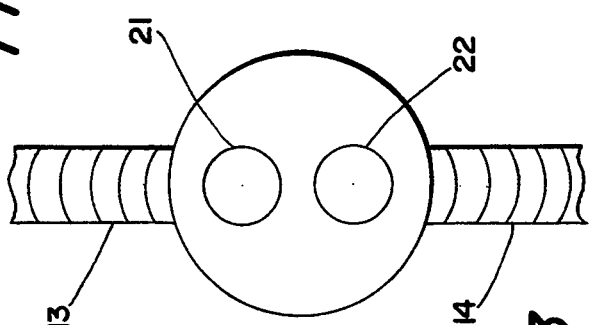
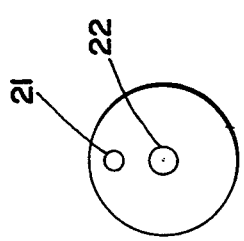

VIBRATING CATHETER

This is a continuation-in-part of Ser. No. 07/885,665, filed May 19, 1992, now abandoned.

BACKGROUND OF THE INVENTION

1. Field of Invention

The present invention is generally directed to removal of blockage of tubular tissue and specifically directed to the dissolution of intravascular thrombi.

2. Brief Description of Prior Art

It is well known that the formation of thrombi (clots) in blood vessels is a serious medical malady. Thrombi are correlated to the formation of plaque buildup in blood vessels and when blockage occurs, it is more a result of the thrombi than of the plaque buildup (which is usually referred to as atherosclerosis when it is involved in arteries).

All thrombi need not be treated interventionally, but in many instances thrombi do, in fact, become life threatening and require removal or at least reduction in size. A thrombus is primarily comprised of red blood cells and fibrin. There are several treatments which could be adapted for the removal of thrombi in vessels which involve intravascular catheters. Most such intravascular catheters have been designed primarily for plaque removal and contain an element that vibrates at ultrasonic frequencies. Representative of such atherectomy catheters are U.S. Pat. Nos. 5,069,664; 4,920,954; 4,898,575 and 4,808,153. Some involve cutting the plaque off of the wall of the vessel using a cutting blade. Some may be adapted to facilitate removal of a thrombus in a vessel. For example, DonMicheal, et al., in U.S. Pat. No. 4,870,953 describe an intravascular catheter having a bulbous head at its distal end which vibrates at ultrasonic frequencies. It is suggested that such a tip might be useful for disintegrating a thrombus. DonMicheal, et al. also teaches the discharge of a radiographic contrast medium from the catheter tip to enable visualization of the cleared vessel. A second cooling solution may be circulated through the catheter to the tip to prevent overheating of the bulbous tip. All the foregoing intravenous catheters have their shortcomings. None are particularly adapted for removing thrombi.

The use of laser catheters for treatment of thrombi is not uncommon, and significant damage to vessels during this treatment have been reported. The use of drugs for the primary dissolution of these clots is extremely common and is often considered the primary treatment of choice when a thrombus is present. These drugs are referred to as thrombolytic agents (meaning clot dissolution or decomposition). The most common thrombolytic agents (drugs) that are used presently in the treatment of vascular thrombosis are such agents as urokinase, streptokinase, TPA, leech saliva and other such pharmaceutical clot dissolving agents. Significant problems such as hemorrhagic complications, early rethrombosis, prolonged infusion times, costs, significant failure rates, etc., are persistent problems with the use of these pharmaceutical agents. To overcome the aforesaid problems with drugs, an intravascular spraying catheter may be placed in or near a thrombus and the clot periodically sprayed (or pulsed) with a thrombolytic agent which facilitates clot dissolution. Using intermittent spraying of thrombolytic agents may enable the use of less drug over a shorter time period to effect for thrombolysis when compared to the more classical approach of allowing the drug to drip in or near the clot. But even this approach requires excessive time and drug amount. In addition, the use of pulsatile injections of thrombolytic agents may result in pieces of the clot fracturing off from the main body of the clot and causing an embolism which is a danger faced by interventionalists performing this procedure. It is, therefore, desirable to provide an improved catheter for delivering thrombolytic agents which reduce the time and amount of pharmaceutical agent required for thrombolysis and which reduces the danger of embolism.

Stiles, in U.S. Pat. No. 4,692,139 (incorporated herein by reference) describes a catheter for removing obstructions from biological ducts which transmits ultrasonic vibrations to the obstruction to facilitate lysis. Stiles' catheter has means for administering a lysing agent and simultaneously administering ultrasonic vibrations to obstructing material forward of the catheter tip. The Stiles catheter has a vibrating probe which probe (when the catheter is deployed within a vessel) projects from the tip of the catheter. There is no teaching of any advantages to be gained by either: (a) vibrating the catheter (as opposed to a probe housed within a catheter); or (b) using low frequencies (frequencies below 1000 Hz). Further, Stiles teaches the use of vibrational frequencies in the range "of at least 60 KHz". The vibrational frequency employed to effect lysis is an important issue. It is noted that at the frequencies suggested by Stiles' teaching, the wavelength of ultrasound in the probe is $$\lambda = \frac{v}{f} < \frac{1000}{f} < \frac{1000}{60,000}$$

or $\lambda < 1/60$ foot. Thus, in Stiles' catheter there are normally many wavelengths of ultrasound between the ultrasonic source and the probe tip. Wherever the probe tip touches the surrounding aspiration tube walls and/or aspirate, energy will be lost due to heating. Thus, it is difficult or impossible to control the amount of ultrasonic vibratory energy reaching the tip of the probe. Depending on the amount of loss of ultrasonic vibrational energy that occurs along the length of the probe (which, of course, depends on the amount of aspirate in the aspirator tube and the amount of mechanical contact between the probe and the surrounding walls) the energy actually delivered to tissue at the probe tip may either ablate or weld tissue, emulsify an obstruction or be insufficient to have any effect on an obstruction.

Lower frequency vibrations (less than 100 Hz) have wavelengths greater than one foot. The amplitude and, therefore the energy of the low frequency vibration delivered to the tip of a catheter is much more predictable at the lower frequencies and enable more accurate dosimetry. This is because the, vibratory loss to surrounding tissue is due to uniform frictional losses along the length of the elongate member (inserted catheter). Stiles' probe, which vibrates at ultrasonic frequencies as noted above, is housed within an aspiration tube where it may unpredictably be loaded by contact with any aspirate that may be present or the surrounding catheter walls. That is, the undesirable coupling of vibratory energy out of the Stiles' probe is unpredictable. It would be desirable to provide an interventional catheter having a structure wherein the vibrating element contacts the tissue along its entire length.

All of the prior art thrombolysis catheters have specified ultrasonic frequencies (above audible frequencies)

when advocating adjunctive vibratory waves to assist thrombolysis. Perhaps this is due to the availability of compact solid state crystals that oscillate or may be driven at these frequencies. Perhaps it is the belief that these frequencies assist in "emulsifying" an obstruction such as a thrombus. Whatever the reason, the present teaching surprisingly shows that the application of low frequency mechanical vibrations facilitate thrombus disintegration. Even more surprisingly, this is true even in the absence of an exogenous lysing agent.

SUMMARY OF THE INVENTION

While the invention is best understood and taught by making reference to the invention in context of a particular application such as the treatment of vascular thrombosis, it is the object of the present invention to provide a catheter (herein alternatively referred to as a "motion catheter" or a "vibrating catheter") that can be placed in a blocked lumen in the body and, by either utilizing the motion of the catheter alone or the catheter motion in combination with the dispensing of a medicament suitable for dissolving such blockage, dislodge or more preferably, dissolve said blockage. This motion catheter, which may be simply a moving wire, can be used alone for blockage removal or with a lysing agent to dissolve the blockage. Most preferably, both motion and dispensing are used in combination to effect blockage removal.

The objects of this invention are achieved, in general, by providing a vibrating wire, or alternatively, a vibrating catheter that has an open lumen for delivery of said lysing agents. The vibrating catheter may have one or more directional channels for delivery of a lysing agent which channel(s) are attached to a pump so that delivery of said lysing agent can be controlled with respect to delivery time and delivery rate of the lysing agent.

Because blockage of lumens in the body are often times visualized with image enhancement devices, the catheter of the present invention is conveniently placed by means of fluoroscopy, ultrasound or the like. The motion catheter may be placed in the body in any tubular tissue in proximity to said blockage so that the motion of the catheter will dislodge or preferably dissolve the blockage.

A specific application of the aforementioned motion catheter is the dissolution of blood clots or thrombi with or without the use of a lysing/thrombolytic agent such as urokinase, streptokinase or a similar lysing agent. If the distal tip of the motion catheter is placed in juxtaposition to a blood clot (proximal, distal, inside or adjacent to the clot), the low frequency (1–5000 Hz) motion of the catheter facilitates the dislodgement by mechanical agitation of the thrombolytic clot. Dissolution may be achieved if the vibrating catheter also dispenses a thrombolytic agent. Usually the thrombi are located in an artery. As a thrombus dissolves, it is desirable that the tip of the motion catheter be moved (with regard to it's original placement/location) to keep the tip in juxtaposition with the clot and to further facilitate the dissolution of the thrombi.

BRIEF DESCRIPTION OF THE DRAWINGS

FIG. 1 is a schematic view of a preferred embodiment of the motion catheter of the present invention.

FIG. 2 is a cross-sectional view of the distal treatment tip of the catheter of FIG. 1 along line 2—2.

FIG. 3 is a cross-sectional view of the motion catheter of FIG. 1 taken near the proximal end of the catheter along line 3—3.

FIG. 4 is a longitudinal cross-sectional view of the proximal end of the motion catheter of FIG. 1 taken along line 4—4.

DESCRIPTION OF THE PREFERRED EMBODIMENT

Figure 5:
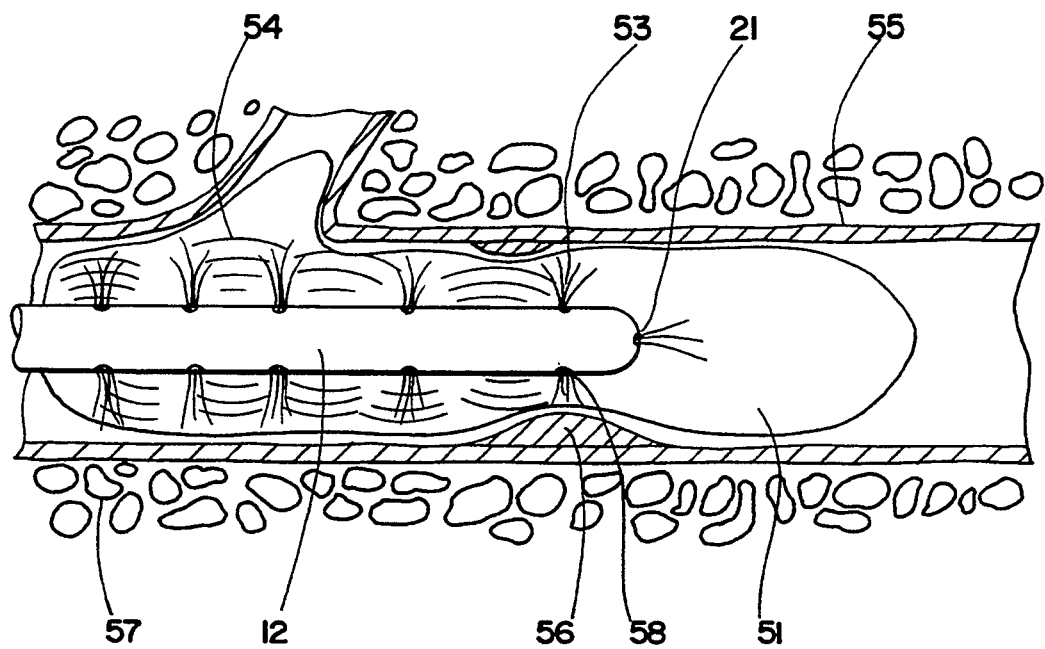
FIG. 5 is a schematic perspective view of the preferred embodiment of the motion catheter of the present invention wherein the distal treatment tip of the catheter of the present invention is embedded in the obstruction (shown in cross-section) causing blockage of the lumen.

Turning now to FIG. 1, a preferred embodiment of the motion catheter of the present invention is generally indicated at the numeral 10. The catheter 10 has a proximal end 11 and a distal or treatment end 12. The proximal end 11 matingly engages a vibrating member 16 which vibrating member 16 is driven by an oscillator 15. The catheter 10 may have one or more lumens extending from the proximal end to the distal end. One lumen, which is optional, is a guidewire lumen which enters the catheter through the guidewire lumen port 13 and exits the catheter through the distal tip 12. A second lumen, having an entry port generally indicated at 14, extends the length of the catheter to the distal tip 12 and is used as a conduit for transporting a lysing agent or other compatible fluid (e.g. saline) from a reservoir (not shown) to the distal tip 12 of the catheter 10.

The distal tip 12 of the catheter 10, which may be radiopaque, is shown in cross-section in FIG. 2. A lysing agent lumen 21 extends the length of the catheter connecting the lysing agent entry port 14 with dispensing holes near the distal tip 12. There may be one or more holes surrounding the tip 12, which holes are in fluid communication with the lysing agent lumen 21. The guidewire lumen 22, which is optional, enables the use of the catheter with a guidewire. The guidewire (not shown) may be introduced into the vessel in which the catheter is to be inserted for removing blockage. The abnormal narrowing or constriction of a passage or lumen such as results from a clot lodged in a blood vessel is called a stenosis. The guidewire is advanced, usually by means of x-ray, until it reaches the point of stenosis. The guidewire may then be either forced through the stenosis or it may terminate at the stenosis. The catheter 10, may then be inserted over the guidewire and advanced so that the distal tip 12 of the catheter is in juxtaposition with the blockage. While for many applications the presence of a guidewire lumen is necessary, for other applications it is not required. A pump (not shown) may be used to force a lysing agent into the lysing agent lumen 21 through the entrance port 14.

It is known in the prior art to be advantageous to have an element within an intravascular catheter capable of vibration at high frequencies. Such catheters normally require the element to vibrate at ultrasonic frequencies to effect the result desired. Accordingly, such catheters employ a titanium wire coupled to an ultrasonic generator such as a piezoelectric crystal which causes the wire to vibrate longitudinally at ultrasonic frequencies. In these instances, the ultrasonic energy is transferred to the medium surrounding the vibrating element and is used to cause cavitation at the tip of the catheter, which cavitation may cause the disruption of the blockage. Alternatively, an ultrasonic transducer may be placed at the tip of the catheter to emit ultrasonic waves laterally therefrom and receive reflections from the walls of the surrounding vessel thereby providing an ultrasonic image of the vessel wall. The use of ultrasonic frequencies produces heat, both along the wall of the catheter and at the tip which requires a cooling fluid. In addition, titanium must be used in order to prevent fracture of the wire. In the present invention, the entire catheter 10 is coupled to a source of vibrational energy 16 driven by an oscillator 15 operating in the range of 2 to 1000 oscillations per second. These low frequency vibrations transmit along the catheter to its distal tip 12 providing a mechanical motion of the tip. Such mechanical motion can be used to mix a lysing agent with a blockage near the distal tip. The vibrating agent 16 (FIG. 1) is inserted into the proximal end of the motion catheter 10 as shown in greater detail in FIG. 4. The proximal end 11 of the catheter 10 matingly engages the oscillating element 16. The oscillating element 16 reciprocates in the direction of the long axis of the catheter 10. Alternatively, the oscillating element 16 may rotate to and fro causing a back and forth rotary motion along the wall of the catheter which is translated to the tip. Or a to-and-fro motion may be used in combination with a back and forth translational motion to effect a wobbling motion at the tip. The use of such motion in combination with the dispensing of a medicament such as a lysing agent at the tip of the catheter is illustrated in FIGS. 5 through 10.

In FIG. 5, the distal tip 12 of catheter 10 is shown advanced into a blood vessel 55. The blood vessel inner wall 55 is surrounded by tissue generally indicated by 57. An obstruction 51 in the vessel is penetrated by the distal treatment tip 12 of the catheter 10. Once tip 12 of the catheter 10 is within the obstruction 51 (such as a blood clot) a lysing agent 53 is dispensed from the holes 58 near the tip of the catheter by means of pumping the lysing agent 53 from a reservoir (not shown) through the lysing agent lumen 21. At the same time, the mechanical motion of the tip, generally indicated at 54, is induced in the distal tip of the catheter by means the vibrating element 16. The combination of lysing agent 53 emanating from holes 58 in the distal tip 12 of the catheter 10 in combination with the vibratory motion 54 of the distal tip of the catheter assists in the penetration of the lysing agent into the obstruction 51, and provides an advantage over prior art.

Figure 6:
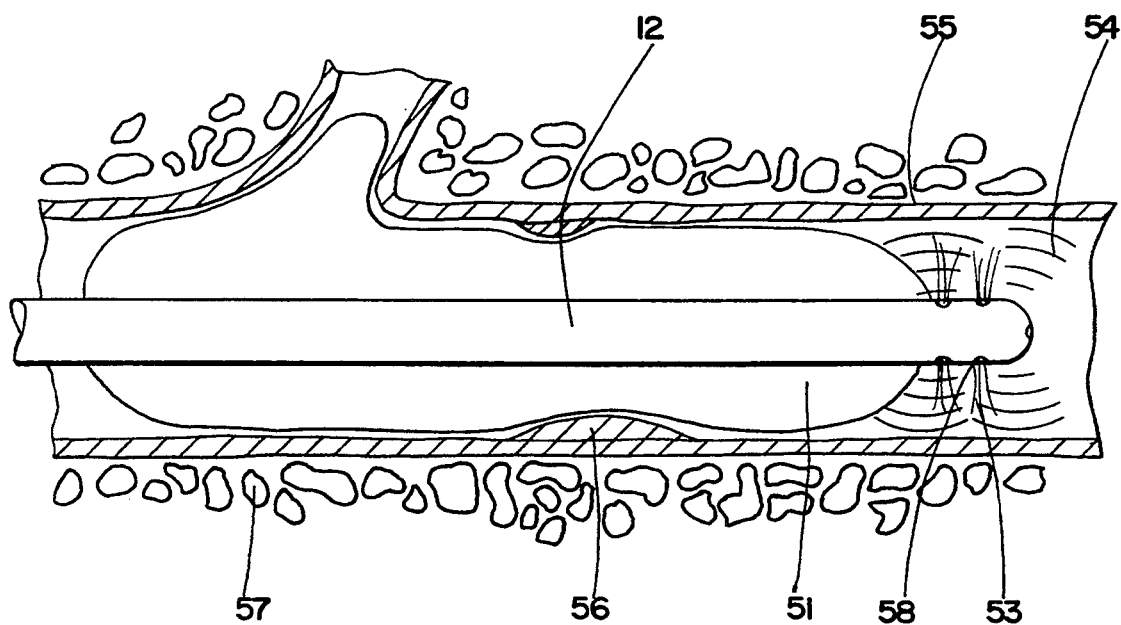
FIG. 6 is a schematic perspective of the preferred embodiment of the present invention shown in FIG. 5 wherein the motion catheter passes through or around the obstruction and the lysing agent (if required) emanates from the most distal portion of the catheter.

Alternatively, the distal tip 12 of the catheter 10 may be inserted into the blockage 51 and passed completely therethrough, as shown in FIG. 6, so that the very distal-most portion of the distal tip 12 extends beyond the obstruction 51. In such an event, motional waves 54 may be used in combination with the release of a lysing agent 53 from holes 58 in the distal tip to facilitate dissolution of the blockage 51. This may be particularly advantageous in the event that plaque 56 is covering a portion of the wall 55 of the vessel.

Figure 7:
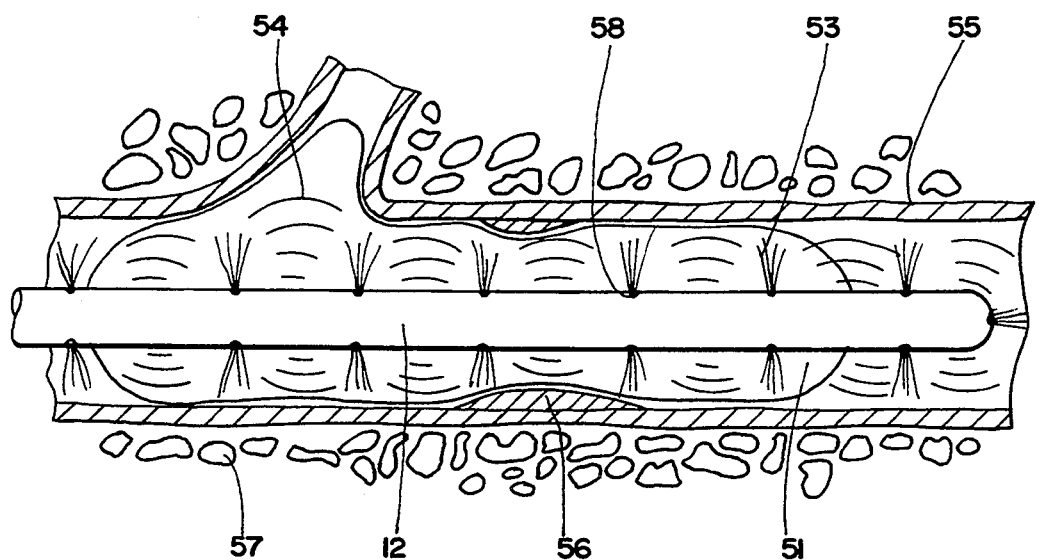
FIG. 7 is a schematic perspective view of the preferred embodiment of the present invention shown in FIG. 5 wherein the distal treatment tip of the catheter protrudes through the clot/obstruction and the lysing agent sprays inside the clot and both proximal and distal to the clot.

As shown in FIG. 7, it is also possible to have a plurality of holes 58 dispensing the lysing agent 53, both distal to the obstruction 51 and interior to the obstruction. Such a combination of vibrational motion and spraying of lysing agent into the blockage facilitates the rapid disruption of the blockage 51.

Figure 8:
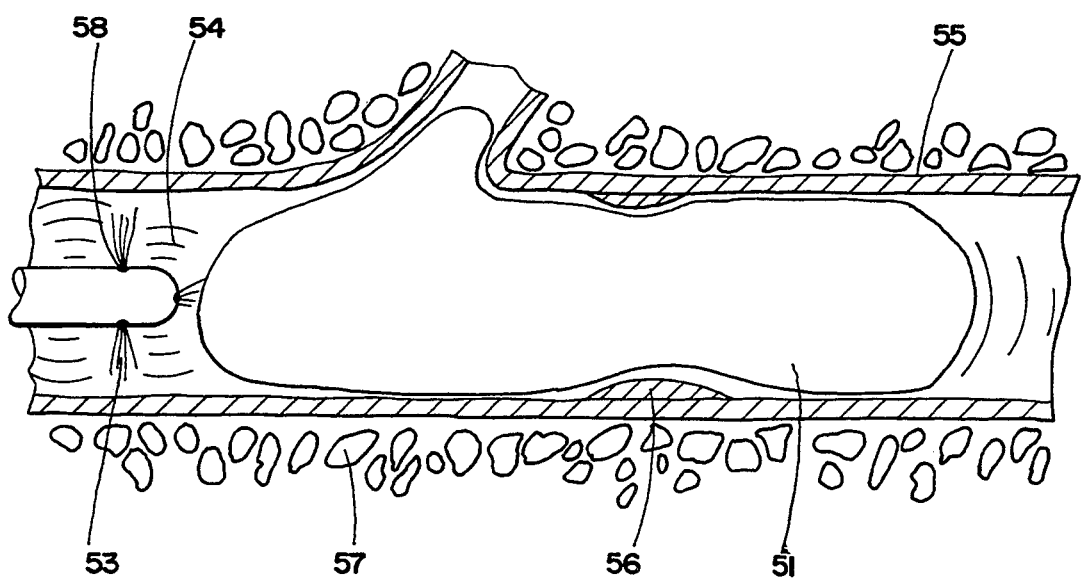
FIG. 8 is a cross-sectional view of the preferred embodiment of the present invention in FIG. 5 wherein the distal treatment tip of the motion catheter is located proximal to the obstruction and the spraying lysing agent delivered from the tip in a direction parallel to the long axis of the catheter.

In FIG. 8, the distal tip ].2 is advanced until it is in juxtaposition with the proximal end of the blockage 51. When the distal tip is in position, the vibrational waves 54 in combination with the release or spraying of lysing agent 53 affect the dissolution of the blockage 51.

Figure 9:
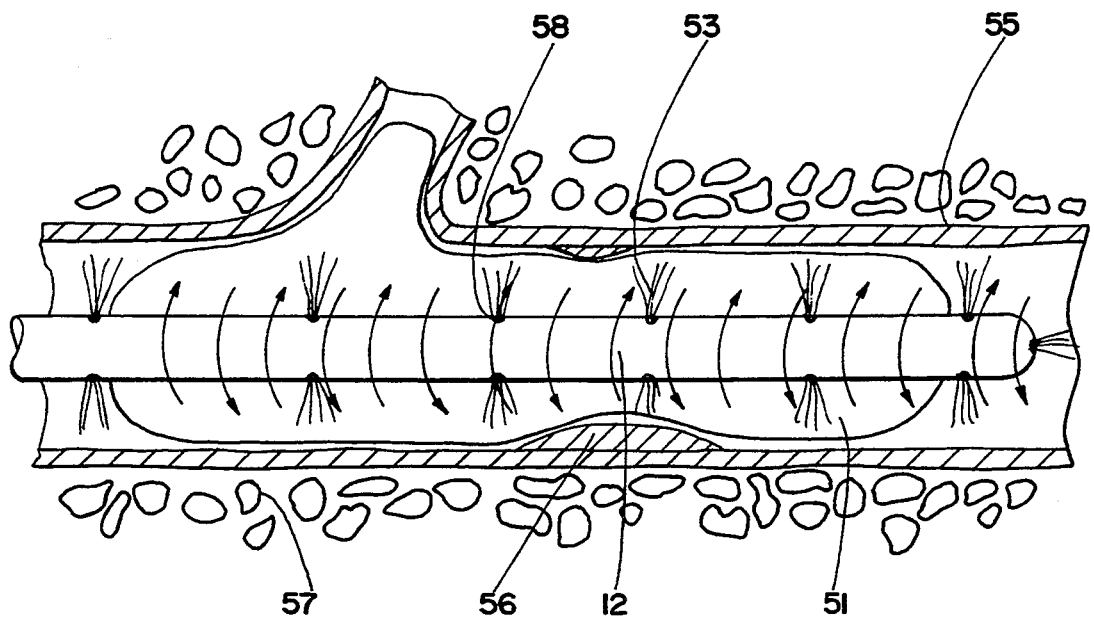
FIG. 9 is a perspective view of the distal tip of the preferred embodiment of the present invention shown in FIG. 5 wherein the motion catheter is rotating or oscillating in a to-and-fro motion while the lysing agent is being dispensed.

Up until now, we've been referring primarily to vibrational motion in the tip of the catheter that is axial oscillatory motion generally in the direction of the axis of the catheter. FIG. 9 shows a rotary motion which may be imparted to the tip of the catheter by applying an oscillating rotary motion to the proximal end of the catheter. The arrows in FIG. 9 show the rotation of various elements of the tip of the catheter with respect to adjacent elements of the catheter. The catheter 10 is a flexible structure and these rotational waves can travel down the catheter changing direction. Such rotary motion, particularly when the tip 12 is embedded within the blockage 51, may be particularly advantageous for facilitating the penetration of lysing agent 53 sprayed from the holes 58 in the distal tip 12 of the catheter 10. The rotational arrows are generally indicated at 58.

Figure 10:
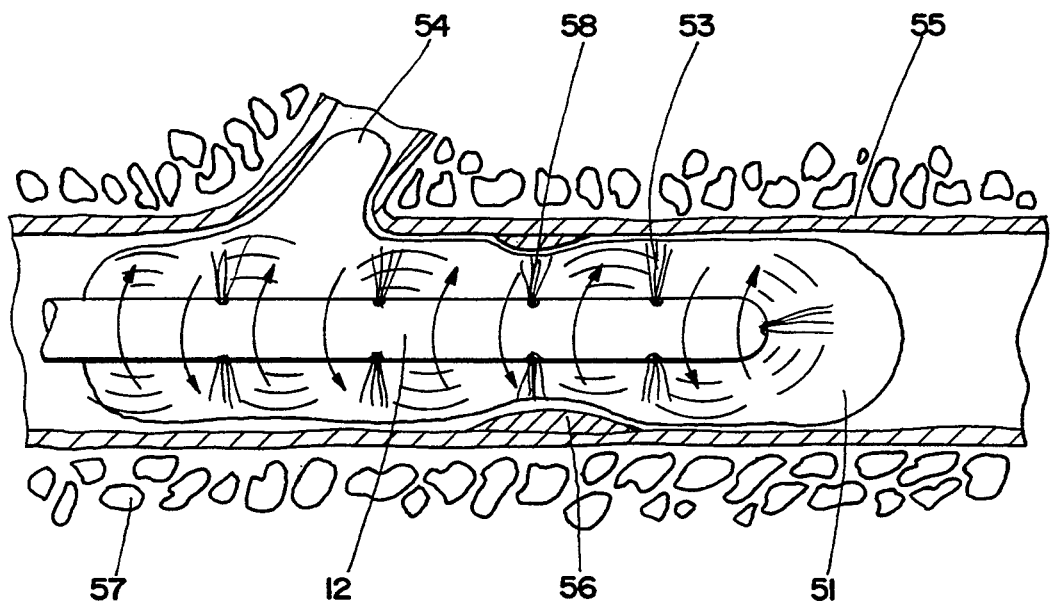
FIG. 10 is a cross-sectional view of the preferred embodiment of the present invention shown in FIG. 5 wherein the lysing agent is dispensed by holes in the distal tip and is directed within and/or under the body of the obstruction.

FIG. 10 shows a translational motion which can be used in combination with the rotary motion of FIG. 9, which combination of motions may cause the tip 12 of the catheter 10 to "wobble" or "wiggle" causing mixing and enabling the lysing agent 53 to more rapidly permeate the obstruction 51 facilitating dissolution thereof.

Figure 11:
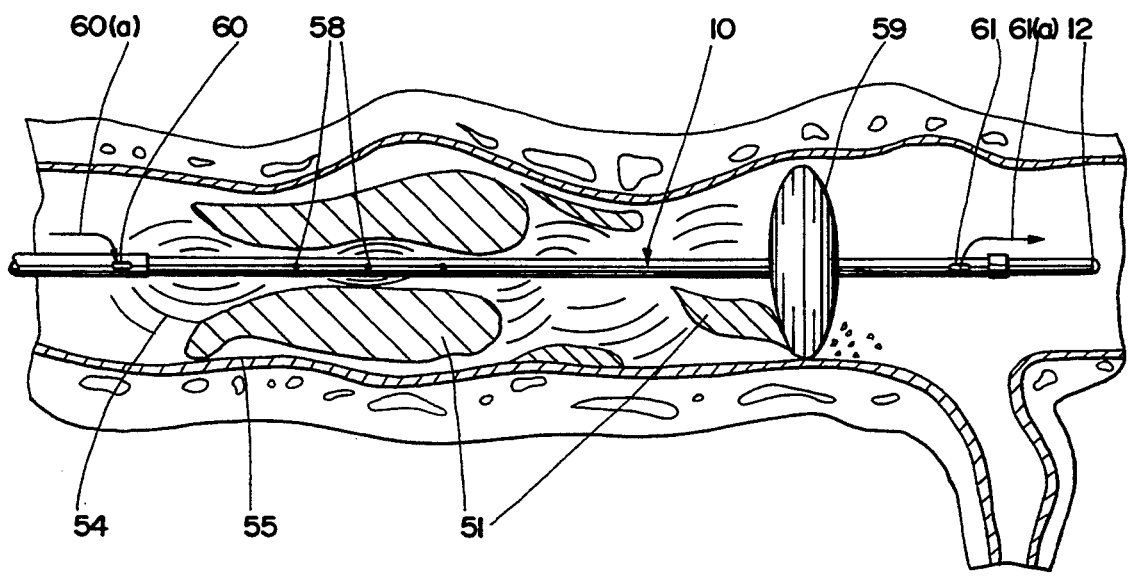
FIG. 11 is a cross-sectional view of a second preferred embodiment of the present invention wherein an inflatable vessel occluder near the distal tip of the catheter blocks the flow of blood around the outside of the catheter thereby forcing the blood to flow through a particle filter housed within a perfusion channel within the catheter.

During the dissolution process, fragments of the obstructing thrombus may break loose and obstruct the vascular system at once or more points remote from the original obstruction. A second preferred embodiment of the catheter of the present invention which is especially designed to prevent the dissemination of such fragments to other points in the vascular system is shown in FIG. 11. In this second preferred embodiment the catheter 10 has a coaxial inflatable member 59 on the outer surface thereof between the holes 58, through which holes lysing agent (not shown) is sprayed, and the distal tip 12 of the catheter 10. A perfusion channel (not shown) housed within the body portion of the catheter 10 is coextensive with the portion of the catheter between fenestrations 60 and 61 in the outer wall of the catheter 10 providing fluid communication therebetween. Blood enters the perfusion channel (not shown) through the proximal fenestration 60 in the direction indicated by arrow 60(a). Any fragments of thrombus entrained in the blood as the blood enters the proximal fenestration 60 will pass into the catheter perfusion channel. A particle filter (not shown) is deployed within the perfusion channel to remove such fragments before the blood exits the perfusion channel through the distal fenestration 61 as indicated by arrow 61(a). The falter (not shown) is in-line with the perfusion channel connecting fenestrations 60 and 61 and can be a polymeric or metallic mesh or "birds nest" or a filter of the type used to remove fat cells frown an aspirate described in Dubrul, et al. U.S. Pat. No. 4,834,703, (incorporated herein by reference). Such a filter must be in-line with the perfusion channel and coextensive with at least a portion thereof to effectively remove fragments of thrombus and any other unwanted particulate debris from the perfusate 60(a) and 61(a).

EXAMPLE

To prove evaluate the effectiveness of the present invention, an in vitro experiment was performed to evaluate the advantage, if any, of using the motion catheter to disburse clots rather than existing technology. Blood clots were created in a test tube. The weight of each clot was measured prior to experimentation. The clots were then treated with Urokinase at a rate of 5000 IU/ml for 5 minutes to a total of 15,000 IU. The clot (thrombus) weights were measured initially and finally to determine the amount of lysing that had taken place. One of the groups (GROUP 1) was used as a control. Nothing was done to the GROUP 1 thrombi except initial and final weighing. Another group (GROUP 2) was treated with the same amount of lysing agent, but the lysing agent was dispersed through the motion catheter while the catheter was being very slowly vibrated; the catheter was placed proximal to the clot in similar fashion as was the aforementioned group. In GROUP 3, the MOTION CATHETER was placed in the clot as in GROUPS 1 & 2, but the Urokinase was pulsed into the clot and no motion was applied to the system. In GROUP 4, the lysing agent was pulsed into the clot as in GROUP 36, but a slow (low frequency) vibratory motion was applied to the MOTION CATHETER. GROUP 5 clots were treated with saline and slow vibration. In GROUPS 2,4 & 5 (GROUPS with a motion applied to the MOTION CATHETER) the amount of lysing of the clot/thrombus was greatly increased as determined by the difference in weight of the clot/thrombus before and after the one hour treatment. Those results are tabulated in Table 1 where the percentage of lysing is the difference between the initial and final weight of the clots divided by the initial weight, the quotient multiplied ×100.

TABLE 1

| GROUP 1 | 4.5% Lysing |
| GROUP 2 | 68% |

TABLE 1-continued

| GROUP 3 | 26% |
| GROUP 4 | 45% |
| GROUP 5 | 45% |

From the foregoing data it is clear that low frequency vibration with administration of a lysing agent (GROUP 2) give the best results. Surprisingly, the GROUP 5 clots (no lysing agent) that were subjected only to a low frequency (1–1000 Hz) vibrating member in the presence of saline exhibited substantial dissociation under the conditions of the experiment. This suggests that the introduction of a simple intravascular wire or similar elongate member vibrating at lower frequencies (<1000 Hz) into a blocked vessel may be useful for disrupting clots.

The aforesaid specification taken in connection with the drawings and the aforementioned experiment sets forth the preferred embodiments of the present invention. The embodiments of the invention disclosed herein are the best modes contemplated by the inventors for carrying out their invention in a commercial environment, although it should be understood that various modification can be accomplished within the scope of the invention.

What we claim is:

1. An apparatus for the removal of an obstruction in tubular tissue of a patient comprising an elongate tubular catheter having a proximal end and a distal end and a body portion therebetween, said body portion having at least two lumens and an outer tissue-contacting surface substantially coextensive therewith, said outer tissue-contacting surface being dimensioned to fit within said tubular tissue and said tissue-contacting surface having at least one lysing agent dispensing opening therein and an inflatable member coextensive and coaxial with at least a portion thereof, said inflatable member being distal to said at least one lysing agent dispensing opening; the proximal end of the catheter being trifurcated to form first, second and third projections, the first projection being in material vibratory communication with said tissue-contacting surface and adapted to receive and matingly engage a vibrating element; the second projection providing an injection port which is in fluid communication with said inflatable member, and said third projection forming a lysing agent injection port which is in fluid communication with at least one lysing agent dispensing opening; and wherein said vibrating element produces translational and/or rotational mechanical vibrations between 1–1000 Hz.

2. The apparatus of claim 1 wherein said tubular tissue is a blood vessel and said obstruction is a blood clot.

3. The apparatus of claim 1 further comprising a reservoir for containing said lysing agent and a pump for metering said lysing agent injection port.

4. A method of removing a clot from an obstructed blood vessel comprising the steps of inserting the apparatus of claim 1 into said obstructed blood vessel and advancing the distal tip of the catheter along the vessel until the inflatable member is beyond the clot, inflating said inflatable member by injecting a fluid into said second projection then dispensing lysing agent into or around the clot while the distal tip is vibrating.

* * * * *